United States Patent
Takagi

(10) Patent No.: US 11,176,638 B2
(45) Date of Patent: Nov. 16, 2021

(54) IMAGE PROCESSING APPARATUS, IMAGE PROCESSING METHOD AND PROGRAM

(71) Applicant: Konica Minolta, Inc., Tokyo (JP)

(72) Inventor: Tatsuya Takagi, Mitaka (JP)

(73) Assignee: KONICA MINOLTA, INC., Tokyo (JP)

( * ) Notice: Subject to any disclaimer, the term of this patent is extended or adjusted under 35 U.S.C. 154(b) by 83 days.

(21) Appl. No.: 16/432,181

(22) Filed: Jun. 5, 2019

(65) Prior Publication Data
US 2019/0378243 A1    Dec. 12, 2019

(30) Foreign Application Priority Data
Jun. 7, 2018    (JP) .............................. JP2018-109121

(51) Int. Cl.
G06K 9/46        (2006.01)
G06T 3/40        (2006.01)
A61B 6/00        (2006.01)

(52) U.S. Cl.
CPC .......... *G06T 3/4053* (2013.01); *A61B 6/5264* (2013.01); *G06K 9/46* (2013.01); *G06T 2200/28* (2013.01)

(58) Field of Classification Search
CPC ..... G06T 3/4053; G06T 2200/28; G06K 9/46; A61B 6/5264

USPC ......................................................... 382/132
See application file for complete search history.

(56) References Cited

U.S. PATENT DOCUMENTS

| | | | |
|---|---|---|---|
| 2008/0137934 A1* | 6/2008 | Sakaguchi | A61B 6/503 382/132 |
| 2009/0110309 A1* | 4/2009 | Sakai | H04N 5/783 382/233 |
| 2012/0059239 A1* | 3/2012 | Yamaguchi | A61B 6/463 600/407 |
| 2016/0235388 A1* | 8/2016 | Zhang | A61B 6/5217 |
| 2018/0197290 A1* | 7/2018 | Kasai | A61B 6/503 |
| 2018/0211132 A1* | 7/2018 | Shiraishi | G06K 9/6215 |
| 2018/0232861 A1* | 8/2018 | Hamauzu | G06T 5/50 |

FOREIGN PATENT DOCUMENTS

JP            2011151430 A        8/2011

* cited by examiner

*Primary Examiner* — Ali Bayat
(74) *Attorney, Agent, or Firm* — Cantor Colburn LLP

(57) ABSTRACT

There is disclosed an image processing apparatus including a hardware processor which generates a highly resolved still image from a plurality of frame images obtained by continuously imaging a moving subject. The hardware processor analyzes each of the plurality of frame images to calculate a feature amount, and determines, on a basis of the calculated feature amount, a reference frame image which becomes a reference when generating the highly resolved still image from the plurality of frame images.

7 Claims, 3 Drawing Sheets

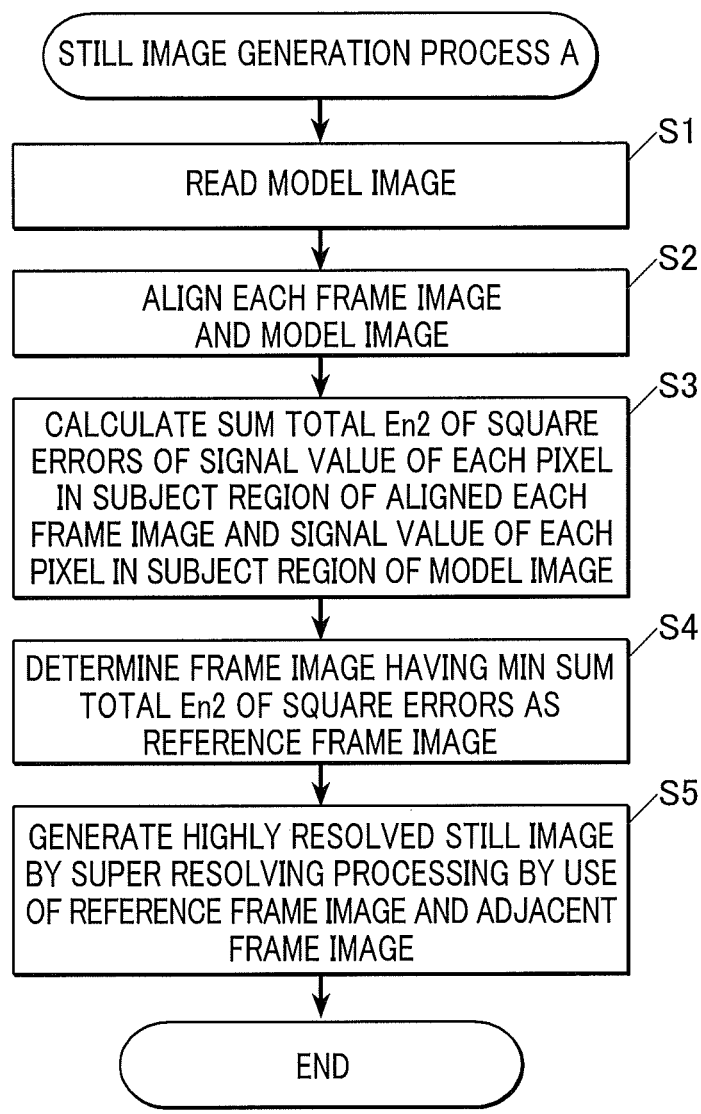

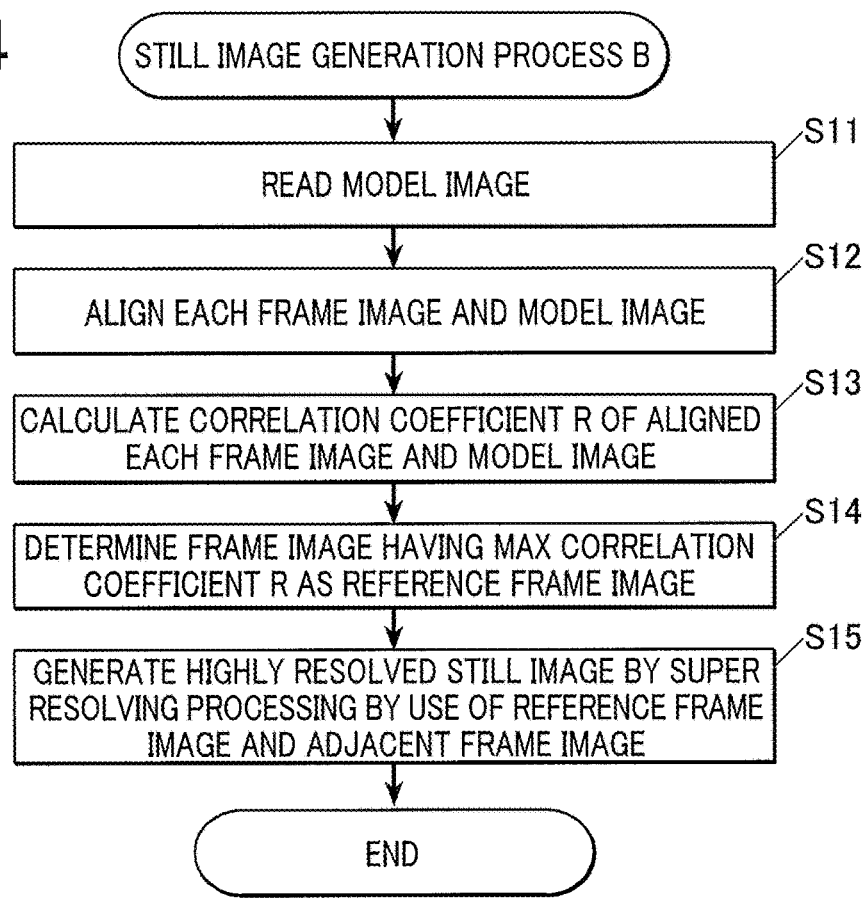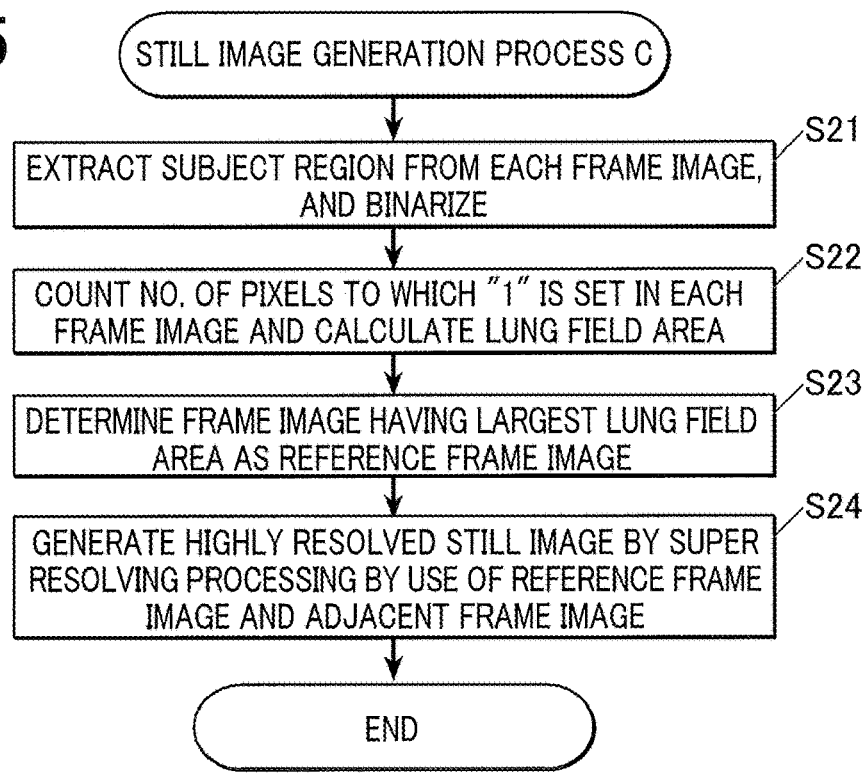

IMAGE PROCESSING APPARATUS, IMAGE PROCESSING METHOD AND PROGRAM

CROSS REFERENCE TO RELATED APPLICATIONS

The present invention claims priority under 35 U.S.C. § 119 to Japanese Application No. 2018-109121 filed Jun. 7, 2018, the entire content of which is incorporated herein by reference.

BACKGROUND

1. Technological Field

The present invention relates to an image processing apparatus, an image processing method and a program.

2. Description of the Related Art

Heretofore, a technology has been known in which a highly resolved still image is prepared from a plurality of frame images which constitute a moving image. For example, it is described in Patent Literature 1 (a publication of Japanese Patent Laid-Open No. 2011-151430) that, when an imaging instruction of a still image is accepted during imaging of a moving image, a target frame image (a reference frame image) corresponding to the imaging instruction is registered in a holder, and also in the holder, at least an adjacent frame image adjacent to the frame image in a time direction is registered as the frame image to be used in super resolving processing. The super resolving processing is performed by using the target frame image and the adjacent frame image which are held in the holder, to generate a highly resolved still image.

However, in the technology described in Patent Literature 1, it is necessary for an operator to specify the reference frame image which becomes a reference when generating the highly resolved still image from the plurality of frame images.

SUMMARY

An object of the present invention is to automatically generate a highly resolved still image without specifying any reference frame image by an operator, when preparing the highly resolved still image from a plurality of frame images which constitute a moving image.

To achieve the above described object, an image processing apparatus which reflects one aspect of the present invention is an image processing apparatus including a hardware processor which generates a highly resolved still image from a plurality of frame images obtained by continuously imaging a moving subject, wherein the hardware processor analyzes each of the plurality of frame images to calculate a feature amount, and determines, on a basis of the calculated feature amount, a reference frame image which becomes a reference when generating the highly resolved still image from the plurality of frame images.

Furthermore, an image processing method which reflects another aspect of the invention is an image processing method in an image processing apparatus which generates a highly resolved still image from a plurality of frame images obtained by continuously imaging a moving subject, the image processing method including analyzing each of the plurality of frame images to calculate a feature amount, and determining, on a basis of the calculated feature amount, a reference frame image which becomes a reference when generating the highly resolved still image from the plurality of frame images.

Additionally, a program which reflects still another aspect of the invention is a program causing a computer for use in an image processing apparatus which generates a highly resolved still image from a plurality of frame images obtained by continuously imaging a moving subject to perform, as a determiner, analyzing each of the plurality of frame images to calculate a feature amount, and determining, on a basis of the calculated feature amount, a reference frame image which becomes a reference when generating the highly resolved still image from the plurality of frame images.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 3 is a flowchart showing a flow of a still image generation process A to be executed by a controller of FIG. 2 in a first embodiment;

FIG. 4 is a flowchart showing a flow of a still image generation process B to be executed by the controller of FIG. 2 in a second embodiment; and FIG. 5 is a flowchart showing a flow of a still image generation process C to be executed by the controller of FIG. 2 in a third embodiment.

DETAILED DESCRIPTION OF EMBODIMENTS

Hereinafter, one or more embodiments of the present invention will be described with reference to the drawings. However, the scope of the invention is not limited to the disclosed embodiments.

First Embodiment

[Configuration of Image Processing System 100]

First, a configuration of a first embodiment will be described.

Figure 1:
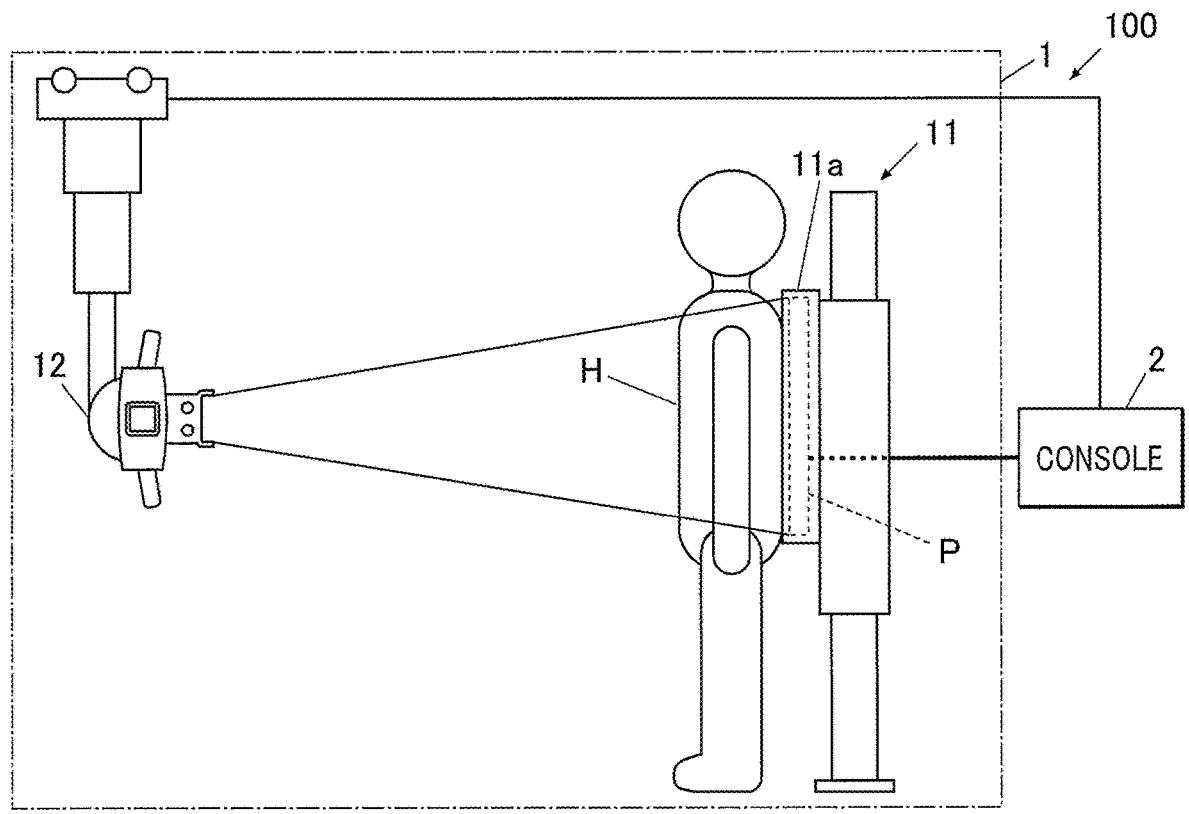
FIG. 1 is a view showing an overall configuration of an image processing system in an embodiment of the present invention.

FIG. 1 is a view showing an overall configuration example of an image processing system 100 according to the present embodiment. As shown in FIG. 1, the image processing system 100 includes an imaging device 1 and a console 2 which are connected to each other so that data can be transmitted and received between the imaging device and the console.

The imaging device 1 is an imaging device which irradiates a subject with radiation, and performs still image capture or moving image capture. In the present embodiment, the capture of the moving image is performed by imaging, as the subject, a diagnosis target region of a human body having periodicity (a cycle), for example, morphological changes of lung expansion and contraction associated with a respiratory motion, heart beating and the like. A series of images obtained by continuously imaging the subject by the moving image capture will be referred to as the moving image. Furthermore, each of a plurality of images which constitute the moving image is referred to as a frame image. Note that in the following embodiments, there is described an example where a chest front is considered as the subject, but the invention is not limited to this example.

The imaging device 1 includes a radiation detector P, an imaging table 11 on which the radiation detector P is loaded, and a radiation generator 12. The radiation detector P can be loaded in a holder 11a of the imaging table 11.

The radiation detector P includes a semiconductor image sensor such as a flat panel detector (FPD), and is provided to face the radiation generator 12 via a subject H. The radiation detector P has, for example, a glass substrate, and includes a plurality of detection elements (pixels) arranged in a matrix manner at a predetermined position on the substrate. In the detector, the radiation (an X-ray) emitted from the radiation generator 12 and transmitted through at least the subject H is detected in response to intensity of the radiation, and the detected radiation is converted to an electric signal and accumulated in the detection elements. Each pixel includes a switching element such as a thin film transistor (TFT). The radiation detector P controls the switching element of each pixel on a basis of image reading conditions input from the console 2, switches reading of the electric signal accumulated in each pixel, and reads the electric signal accumulated in each pixel, to acquire image data. Then, the radiation detector P outputs the acquired image data to the console 2.

The radiation generator 12 is disposed at a position which faces the radiation detector P via the subject H, and irradiates the radiation detector P loaded in the holder 11a with the radiation via a patient as the subject H on the basis of radiation irradiation conditions input from the console 2, to perform the imaging.

The console 2 outputs imaging conditions such as the radiation irradiation conditions and the image reading conditions to the imaging device 1, and controls operations of radiation imaging and reading of a radiation image which are performed by the imaging device 1. Furthermore, the console also functions as an image processor which processes the radiation image acquired by the imaging device 1.

Figure 2:
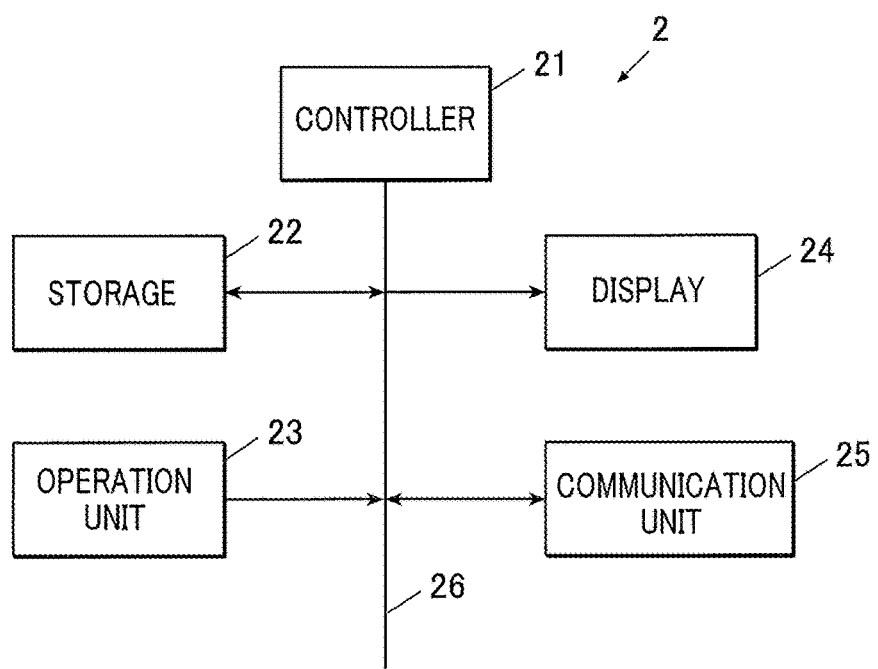
FIG. 2 is a block diagram showing a functional configuration of a console of FIG. 1.

As shown in FIG. 2, the console 2 includes a controller 21, a storage 22, an operation unit 23, a display 24, and a communication unit 25, and the respective units are connected via a bus 26.

The controller 21 includes a central processing unit (CPU), a random access memory (RAM) and others. The CPU of the controller 21 reads a system program and various processing programs stored in the storage 22 in response to an operation of the operation unit 23, develops the program in the RAM, and controls an operation of each unit of the console 2, and the radiation irradiating operation and the reading operation of the imaging device 1 in a centralized manner according to the developed program. Furthermore, the controller 21 executes various processes including the still image generation process A and the others as described later by use of the still image or the moving image transmitted from the radiation detector P of the imaging device 1.

The storage 22 includes a nonvolatile semiconductor memory, hard disk and others. The storage 22 stores various programs to be executed by the controller 21, parameters required for the execution of the processing by the program, or data of processing results or the like. Each program is stored in a form of a readable program code, and the controller 21 successively executes the operation according to the program code.

Furthermore, the storage 22 stores the imaging conditions (the radiation irradiation conditions and the image reading conditions) corresponding to respective imaging regions. Additionally, the storage 22 stores imaging order information transmitted from an unshown radiology information system (RIS) or the like. The imaging order information includes patient information, inspection information (an inspection ID, the imaging region (also including an imaging direction), an inspection date, a type of still image capture or moving image capture, etc.) and the like.

Additionally, the storage 22 associates the still image or the moving image acquired by the imaging, and the image generated by image processing with the patient information or the inspection information, and stores the images.

In addition, the storage 22 stores a model image (details will be described later).

The operation unit 23 includes a keyboard having a cursor key, numeric input keys, various function keys and the like, and a pointing device such as a mouse, and outputs, to the controller 21, an instruction signal input by a key operation to the keyboard, or a mouse operation. Furthermore, the operation unit 23 may include a touch panel in a display screen of the display 24. In this case, the instruction signal input via the touch panel is output to the controller 21. Additionally, the operation unit 23 also includes an exposure switch to instruct kymography to the radiation generator 12.

The display 24 includes a monitor of a liquid crystal display (LCD), a cathode ray tube (CRT) or the like, and displays an input instruction, data or the like from the operation unit 23 in accordance with an instruction of a display signal input from the controller 21.

The communication unit 25 has an interface to transmit and receive data to and from the radiation generator 12 and the radiation detector P. Note that communication of the console 2 with the radiation generator 12 and the radiation detector P may be wired communication or wireless communication.

Furthermore, the communication unit 25 includes a LAN adaptor, a modem, a terminal adapter (TA) and others, and controls the data transmission and reception with the unshown RIS or the like connected to a communication network.

[Operation of Image Processing System 100]

When the imaging order information of an imaging target is selected by the operation unit 23 of the console 2 in a state where the radiation detector P is set to the holder 11a of the imaging device 1, the imaging conditions (the radiation irradiation conditions and the radiation image reading conditions) corresponding to the selected imaging order information are read from the storage 22, transmitted to the imaging device 1, and set to the imaging device 1. When the subject H is positioned and the exposure switch is depressed, in the imaging device 1, the subject is irradiated with the radiation by the radiation generator 12, and the still image or each of a plurality of frame images of the moving image is acquired by the radiation detector P and transmitted to the console 2.

Upon receiving the still image or the moving image from the radiation detector P by the communication unit 25 of the console 2, the controller 21 associates the received still image or moving image with the patient information or the inspection information to store the image in the storage 22. Furthermore, the controller 21 executes the still image generation process A based on the received moving image.

FIG. 3 is a flowchart showing a flow of the still image generation process A. The still image generation process A is executed by cooperation with the controller 21 and the program stored in the storage 22.

First, the controller 21 reads the model image from the storage 22 (step S1).

Here, the model image is an image which becomes a model of the still image generated from the plurality of frame images which constitute the moving image, and for a medical image in which the diagnosis target region of the human body is considered as the subject as in the present embodiment, there is used the model of the still image for use in still image diagnosis. In the still image diagnosis, the diagnosis is performed by the still image of the subject in a predetermined state (e.g., a maximum inspiratory level or a maximum expiratory level, when the subject is a chest). Therefore, for example, the image of the subject in the predetermined state can be used as the model image. Furthermore, when comparative reading is performed, it is preferable to generate, as a comparison target, a still image in the same state as in a still image acquired by imaging the same region of the same patient in the past (or a still image generated from a moving image acquired by imaging the same region of the same patient in the past). Consequently, as the model image, for example, there may be used the still image acquired by imaging the same region of the same patient in the past (or the still image generated from the moving image acquired by imaging the same region of the same patient in the past).

Next, the controller 21 aligns each frame image of the moving image and the model image (step S2).

In the step S2, first, a subject region is extracted from each frame image and the model image. There are not any special restrictions on an extraction technique of the subject region, and a known technique can be used. For example, first, the frame image is divided into a plurality of small regions, and an average value of pixel signal values included in each small region is obtained as a threshold value Th1 for each small region. Next, for each small region, a pixel having a signal value lower than the threshold value Th1 is detected as the subject region. Next, an average signal value of the subject region obtained from each small region is obtained as a threshold value Th2. Next, a pixel having a signal value lower than the threshold value Th2 in the whole image is detected as the subject region. Then, a boundary line between the region and a region out of an irradiation field is obtained, and a region from the boundary line to an image end closer to the boundary line is removed as the region out of the irradiation field. Consequently, the subject region can be extracted (see a publication of Japanese Patent Laid-Open No. 2003-190129).

Next, while moving and/or expanding or contracting each frame image, a sum total En1 of square errors E1 (Equation 1) of a signal value Fn(x,y) of each pixel in the subject region and a signal value Ip(x,y) of each pixel in the subject region of the model image is calculated, and x'=xn, y'=yn, k=kn are calculated in which the sum total En1 is minimum:
$$E1=[Fn(k(x-x'),k(y-y'))-Ip(x,y)]^2 \ldots \text{Equation (1)},$$
in which x' or y' indicates a movement amount of a position, and k indicates an enlargement/reduction amount.

Next, the controller 21 calculates a sum total En2 of square errors E2 (Equation 2) of a signal value of each pixel in the subject region of each of the respective aligned frame images and a signal value of each pixel in the subject region of the model image (step S3):

$$E2=[Fn(kn(x-xn),kn(y-yn))-Ip(x,y)]^2 \quad \text{Equation (2).}$$

Next, the controller 21 compares the sum totals En2 calculated from the respective frame images, and determines the frame image having the minimum sum total En2 as a reference frame image (step S4).

Then, the controller 21 performs super resolving processing by use of the reference frame image and at least one frame image adjacent to the reference frame image in a time direction, and generates a highly resolved still image (step S5), thereby ending the still image generation process A.

In the super resolving processing, with reference to not only pixel information that the reference frame image has but also pixel information that the frame image adjacent in the time direction has, the controller generates the still image (i.e., the highly resolved still image) having a resolution higher than a resolution of the reference frame image (the frame image which constitutes the moving image) while effectively removing noise included in the reference frame image. There are not any restrictions on a specific technique of the super resolving processing. For example, a technique described in the following reference literature 1 or any other known technique may be used (Reference Literature 1: Dennis Mitzel, "Video Super Resolution using Duality Based TV-L1 Optical Flow", 2009 in DAGM-Symposium).

The still image generated by the still image generation process A is associated with the patient information and inspection information of the original moving image and stored in the storage 22.

Thus, in the first embodiment, the controller 21 determines, as the reference frame image for use in the super resolving processing, the frame image having the smallest sum total of the square errors of the frame image from the model image among the plurality of frame images which constitute the moving image. Therefore, it is possible to automatically generate the highly resolved still image in a state of the subject which is similar to a state of the model image, without specifying the reference frame image from the moving image by an operator.

Second Embodiment

Hereinafter, a second embodiment of the present invention will be described.

In the first embodiment, it is described that each frame image of a captured moving image is analyzed to calculate square errors of the image from a model image, and a reference frame image is automatically determined on a basis of the square errors calculated from respective frame images. On the other hand, in a second embodiment, there is described an example where each frame image of a moving image obtained by imaging a chest front is analyzed, to calculate a correlation coefficient with a model image, and a reference frame image is automatically determined on a basis of the correlation coefficient calculated from each frame image.

In the second embodiment, a program to execute a still image generation process B described later is stored in a storage 22.

The other configuration in the second embodiment is similar to the configuration described in the first embodiment with reference to FIG. 1 and FIG. 2, and hence, the description is used. Furthermore, in an operation of an image processing system 100 in the second embodiment, an operation of an imaging device 1 is similar to the operation described in the first embodiment, and hence, the description is used. Hereinafter, description will be made as to the still image generation process B executed in a console 2 on a basis of a moving image received from the imaging device 1.

FIG. 4 is a flowchart showing a flow of the still image generation process B. The still image generation process B is executed by cooperation of a controller 21 and a program stored in a storage 22.

First, the controller 21 reads a model image from the storage 22 (step S11).

The processing in the step S11 is similar to the processing described in the step S1 of FIG. 3, and hence, the description is used.

Next, the controller 21 aligns each frame image of a moving image and the model image (step S12).

The processing in the step S12 is similar to the processing described in the step S2 of FIG. 3, and hence, the description is used.

Next, the controller 21 calculates a correlation coefficient R of each frame image and the model image which are aligned (step S13).

The correlation coefficient R can be obtained by Equation (3):

[Expression 1]

$$R = \frac{\sum_x \sum_y Fn(kn(x-xn), kn(y-yn))lp(x,y)}{\sqrt{\sum_x \sum_y Fn(kn(x-xn), kn(y-yn))^2 + \sum_x \sum_y lp(x,y)^2}}$$ Equation (3)

Next, the controller 21 compares the correlation coefficients R calculated for the respective frame images, and determines the frame image having the maximum correlation coefficient R as a reference frame image (step S14).

Then, the controller 21 performs super resolving processing by use of the reference frame image and at least one frame image adjacent to the reference frame image in a time direction, and generates a highly resolved still image (step S15), thereby ending the still image generation process B.

The processing of the step S15 is similar to the processing described in the step S5 of FIG. 3, and hence, the description is used.

The still image generated by the still image generation process B is associated with patient information and inspection information of the original moving image and stored in the storage 22.

Thus, in the second embodiment, the controller 21 determines, as the reference frame image for use in the super resolving processing, the frame image having the largest correlation coefficient with the model image among the plurality of frame images which constitute the moving image. Therefore, it is possible to automatically generate the highly resolved still image in a state of the subject which is similar to a state of the model image, without specifying the reference frame image from the moving image by an operator.

Third Embodiment

Hereinafter, a third embodiment of the present invention will be described.

In the first and second embodiments, it is described that each frame image of a captured moving image is analyzed to calculate a feature amount (a square error or a correlation coefficient) indicating a similarity to a model image, and a reference frame image is automatically determined on a basis of the feature amount calculated from each frame image. On the other hand, in the third embodiment, there is described an example where each frame image of a moving image obtained by imaging a chest front is analyzed, to calculate an area of a lung field, and a reference frame image is automatically determined on a basis of the lung field area calculated from each frame image.

In the third embodiment, a program to execute a still image generation process C described later is stored in a storage 22.

The other configuration in the third embodiment is similar to the configuration described in the first embodiment with reference to FIG. 1 and FIG. 2, and hence, the description is used. Furthermore, in an operation of an image processing system 100 in the third embodiment, an operation of an imaging device 1 is similar to the operation described in the first and second embodiments, and hence, the description is used. Hereinafter, description will be made as to the still image generation process C executed in a console 2 on a basis of a moving image received from the imaging device 1.

FIG. 5 is a flowchart showing a flow of the still image generation process C. The still image generation process C is executed by cooperation of a controller 21 and a program stored in the storage 22.

First, the controller 21 extracts a subject region from each frame image of the received moving image and binarizes the subject region (step S21).

The subject region can be extracted by using, for example, the technique described in the step S2 of FIG. 3. Furthermore, in the binarization, for example, "1" is set to a pixel having a signal value which is 0.8 times or more as large as a maximum signal value in the subject region, and "0" is set to a signal value which is less than 0.8 times. A lung field region can be extracted by extracting the pixel region to which "1" is set.

Next, the controller 21 counts a number of pixels to which "1" is set in the step S21 in each frame image and calculates a lung field area (step S22).

Next, the controller 21 determines, as a reference frame image, a frame image having the largest lung field area, i.e., a maximum inspiratory level (step S23).

Note that a frame image having the smallest lung field area, i.e., a maximum expiratory level may be determined as the reference frame image.

Here, in still image diagnosis of a chest front, the diagnosis is generally performed by using the still image having the maximum inspiratory level or the maximum expiratory level. Consequently, in the step S23, the frame image having the maximum inspiratory level or the maximum expiratory level is determined as the reference frame image.

Then, the controller 21 performs super resolving processing by use of the reference frame image and at least one frame image adjacent to the reference frame image in a time direction, and generates a highly resolved still image (step S24), thereby ending the still image generation process C.

The super resolving processing is similar to the processing described in the step S5 of FIG. 3, and hence, the description is used.

The still image generated by the still image generation process C is associated with patient information and inspection information of the original moving image and stored in the storage 22.

Thus, in the third embodiment, the controller 21 specifies the frame image having the maximum inspiratory level or the maximum expiratory level from the moving image of the chest front and determines the frame image as the reference frame image for use in the super resolving processing. Therefore, it is possible to automatically generate the highly resolved still image having the maximum inspiratory level or the maximum expiratory level, without specifying the frame image having the maximum inspiratory level or the maximum expiratory level from the moving image by an operator.

Note that there is described an example where the lung field area is obtained from each frame image by the binarization in the above still image generation process C, but a lung field region may be recognized from each frame image, and a number of pixels in the recognized lung field region may be counted to obtain the lung field area. The lung field region may be recognized by using any known technique. For example, a threshold value is obtained from a histogram of a signal value of each pixel of the frame image by judgment analysis, and a region of a high signal is primarily extracted as a candidate for the lung field region from this threshold value. Next, an edge is detected in a vicinity of a border of the primarily extracted lung field region candidate, and a point at which the edge becomes largest in the vicinity of the boundary is extracted along the boundary, so that the lung field region can be recognized.

Furthermore, it is described that the reference frame image is determined on a basis of the lung field area of each frame image in the above still image generation process C, but a frame image in which a position of a lower end of the lung field region is lowest or highest may be determined as the reference frame image. Thus, the frame image in which the lower end position of the lung field region is lowest is determined as the reference frame image, so that the frame image having the maximum inspiratory level can be determined as the reference frame image. Furthermore, the frame image in which the lower end position of the lung field region is highest is determined as the reference frame image, so that the frame image having the maximum expiratory level can be determined as the reference frame image. Note that the lower end position of the lung field region can be obtained by specifying the lung field region by the above described binarization or recognition of the lung field region and acquiring, for example, a coordinate of the lowest end of the specified lung field region.

As described above, the controller 21 of the console 2 analyzes each of the plurality of frame images acquired by the imaging device 1 to calculate a feature amount, determines, on a basis of the calculated feature amount, the reference frame image which becomes a reference when generating the highly resolved still image from the plurality of frame images by the super resolving processing, and executes the super resolving processing by use of the determined reference frame image and the frame image adjacent to the reference frame image in the time direction.

Therefore, it is possible to automatically generate the highly resolved still image from the moving image, without specifying the reference frame image from the moving image by the operator.

Note that the above described content in each embodiment is merely one preferred example of the present invention, and the present invention is not limited to this example.

For example, in the above embodiments, there is described an example where the present invention is applied to the chest front image, but the present invention may be applied to an image obtained by imaging a chest side surface or another subject other than the chest.

Additionally, in the above embodiments, there is described a case where the console 2 which controls the imaging device 1 has the function of the image processor, but the image processor may be separate from the console.

Furthermore, for example, in the above description, there is disclosed an example where a nonvolatile memory or the like such as a hard disk or a semiconductor is used as a computer readable medium of the program according to the present invention, but the present invention is not limited to this example. A portable recording medium such as a CD-ROM can be applied as another computer readable medium. Alternatively, a carrier wave is also applied as a medium which provides data of the program according to the present invention via a communication line.

Additionally, a detailed configuration and a detailed operation of each apparatus that constitutes the image processing system can be appropriately changed without departing from the gist of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-109121, filed on Jun. 7, 2018, is incorporated herein by reference in its entirety.

What is claimed is:

1. An image processing apparatus comprising a hardware processor which generates a highly resolved still image from a plurality of frame images obtained by continuously imaging a moving subject, wherein the hardware processor analyzes each of the plurality of frame images to calculate a feature amount, and determines, on a basis of the calculated feature amount, a reference frame image which becomes a reference when generating the highly resolved still image from the plurality of frame images,
   wherein the plurality of frame images are a plurality of frame images obtained by continuously imaging a chest with radiation, and
   the feature amount is an area of a lung field region or a lower end position of a lung field region.

2. The image processing apparatus according to claim 1, wherein the feature amount is a square error from a model image which becomes a model of the generated still image.

3. The image processing apparatus according to claim 1, wherein the feature amount is a correlation coefficient with a model image which becomes a model of the generated still image.

4. The image processing apparatus according to claim 1, wherein
   the feature amount is the area of the lung field region.

5. The image processing apparatus according to claim 1, wherein
   the feature amount is the lower end position of the lung field region.

6. An image processing method in an image processing apparatus which generates a highly resolved still image from a plurality of frame images obtained by continuously imaging a moving subject, the image processing method comprising:
   analyzing each of the plurality of frame images to calculate a feature amount, and determining, on a basis of the calculated feature amount, a reference frame image which becomes a reference when generating the highly resolved still image from the plurality of frame images,
   wherein the plurality of frame images are a plurality of frame images obtained by continuously imaging a chest with radiation, and
   the feature amount is an area of a lung field region or a lower end position of a lung field region.

7. A program stored on a non-transitory medium causing a computer for use in an image processing apparatus which generates a highly resolved still image from a plurality of frame images obtained by continuously imaging a moving subject to perform, as a determiner, analyzing each of the plurality of frame images to calculate a feature amount, and determining, on a basis of the calculated feature amount, a reference frame image which becomes a reference when generating the highly resolved still image from the plurality of frame images, wherein the plurality of frame images are a plurality of frame images obtained by continuously imaging a chest with radiation, and the feature amount is an area of a lung field region or a lower end position of a lung field region.

\* \* \* \* \*